United States Patent
Traina

Patent Number: 6,148,659
Date of Patent: Nov. 21, 2000

[54] GAS CONCENTRATION MONITOR HAVING A BRIDGE CONFIGURED FLOW SYSTEM

[76] Inventor: John E. Traina, 303 N. Rose Dr., Glenshaw, Pa. 15116

[21] Appl. No.: 09/168,819
[22] Filed: Oct. 8, 1998
[51] Int. Cl.⁷ .......................... G01N 31/06; G01N 25/56; G01N 7/00
[52] U.S. Cl. .......................... 73/25.01; 73/23.29; 73/23.2; 422/88; 422/93
[58] Field of Search .................. 73/25.01, 25.05, 73/23.29, 30.02, 30.03, 30.04, 23.2; 422/88, 93

[56] References Cited

U.S. PATENT DOCUMENTS

| | | | |
|---|---|---|---|
| 2,001,865 | 5/1935 | Brandl | 265/44 |
| 2,217,642 | 10/1940 | Luhrs | 265/44 |
| 2,728,219 | 12/1955 | Martin | 73/30 |
| 3,237,181 | 2/1966 | Palmer | 340/237 |
| 3,610,023 | 10/1971 | Ageikin et al. | 73/27 |
| 4,399,687 | 8/1983 | Collins | 73/23 |
| 4,407,153 | 10/1983 | Furlong et al. | 73/23 |
| 4,507,875 | 4/1985 | Hirsch et al. | 34/44 |
| 4,527,417 | 7/1985 | Pravda | 73/23 |
| 4,677,841 | 7/1987 | Kennedy | 73/30 |
| 4,724,700 | 2/1988 | Jaasma | 73/29 |
| 4,891,629 | 1/1990 | Gajjar et al. | 340/632 |
| 5,297,419 | 3/1994 | Richardson | 73/25.03 |
| 5,297,432 | 3/1994 | Traina et al. | 73/886.34 |
| 5,804,703 | 9/1998 | Wind et al. | 73/25.01 |
| 5,948,965 | 9/1999 | Upchurch et al. | 73/23.31 |

*Primary Examiner*—Hezron Williams
*Assistant Examiner*—J. David Wiggins
*Attorney, Agent, or Firm*—Buchanan Ingersoll, P.C.

[57] ABSTRACT

A gas concentration monitor has a pneumatic bridge having two parallel flowpaths containing a first conduit leg and a second conduit leg connected to an input line. Each leg has an entry orifice and an exit orifice through which a portion of the gas sample flows. Orifices need not be of equal size and or kept at the same temperature. A pump is connected to both legs for drawing the sample through the bridge. A condenser or absorber which removes the gas whose concentration is being determined is connected to the first leg between the entry orifice and the exit orifice. A differential pressure gauge measures the differential pressure between the first leg and the second leg which differential pressure changes due to removal of the target gas of measurement interest from the other gas fraction passing through the bridge towards discharge from the bridge. From that measurement one can calculate the concentration in the sample of the gas that was removed by the condenser or absorber.

25 Claims, 2 Drawing Sheets

GAS CONCENTRATION MONITOR HAVING A BRIDGE CONFIGURED FLOW SYSTEM

FIELD OF INVENTION

The invention relates to an apparatus and method for determining the concentration of a selected gas in a flowing gas stream.

BACKGROUND OF THE INVENTION

Conventional gas analyzers have been used for many purposes including measuring gas concentration of gases in a gas stream. Such measurements often are used to measure emissions from furnaces. That information can be used to determine the overall efficiency of the boiler as a heat producing device and to show compliance with environmental regulations.

An important category of gas sampling relates to the compliance monitoring requirements enforced by the United States Environmental Protection Agency (EPA). Many sources of air pollution, such as fossil fuel power plants, incinerators, metal smelters, and cement kilns are required to monitor levels of certain gaseous species that are released into the atmosphere. These species include sulfur dioxide, nitrogen oxide, carbon monoxide, carbon dioxide and oxygen.

The gas streams to be monitored typically have certain intrinsic characteristics which complicate testing. For example, they generally contain 6% to 20% by volume of evaporated moisture. It may be necessary to remove that moisture or know the amount of moisture present before further analysis can be done.

The conventional practice in emissions monitoring has been to insert a probe into the stack to draw off a gas sample. The sample is then directed to a gas analyzer at a remote location. This is necessary because conventional monitors would be adversely affected by the environmental conditions at the stack which could include wide temperature ranges from well below freezing to over 100° F., high winds and particulates in the air. In my U.S. Pat. No. 5,297,432 I disclose a vacuum dilution extraction gas sampling method which relies upon vacuum transport of the gas sample to a remote analyzer. In these monitoring environments the amount of gas to be measured typically is in quantities of a few parts per million. Hence, the analyzer must be quite sensitive.

In U.S. Pat. No. 4,724,700, Jasma discloses a differential flow gas analyzer. The gas sample is filtered and directed through a first orifice. Then the sample is passed through a condenser and a drying column to remove moisture. The dry gas sample is then directed through a second orifice. Jasma measures the flow rate of the gas sample before the second condensing step and after that step. Then, he uses the flow rates to determine the concentration of the moisture removed from the sample.

Hirsch et al. in U.S. Pat. No. 4,507,078 discloses a device for determining the concentration of condensable vapor in a flowing gas stream. The gas sample is passed through a condenser and then through a gas flow meter at the discharge of the gas condenser. The gas samples are drawn in such a manner that the flow rate into the condenser is known. The amount of condensable vapor concentration is determined by comparing the flow of the dry gas sample with the known volumetric flow to the condenser. One problem with the methods disclosed by Hirsch and Jasma is that they are not suitable for measuring low concentrations of the gas of interest in the sample. This is true because the method relies upon finding a difference between the flow rates at two distinct points. Since the sensitivity of flow meters available in the marketplace is limited, relying on the difference between two such readings makes it very difficult to determine the gas concentration if 0.01% or less of the sample is the gas of interest. Hence, these systems are not suitable for emissions monitoring in several industries.

There has long been a need for a simple yet effective gas concentration monitor that employs well-established technology in a cost effective reliable manner. This monitor should be capable of measuring a wide range of concentration in the order of 50% to less than one hundred parts per million.

SUMMARY OF THE INVENTION

I provide a gas concentration monitor having a gas flow bridge configuration containing two legs in the form of gas flow conveying conduits. Both legs are connected to an input line. Each leg has an entry orifice and an exit orifice through which a portion of the gas sample flows. A condenser or absorber is provided in one leg of the bridge. The condenser or absorber removes from the sample the gas whose concentration is desired to be measured. A differential pressure gauge is connected between the first leg and the second leg at locations between the entry orifice and exit orifice of each leg. Because the condenser or absorber removes the gas of interest from the first leg, the pressure in that leg would be lower than the pressure in the second leg. From the differential pressure between the two legs one can calculate the quantity or concentration of the gas which has been removed. I further provide at least one temperature measuring device to assure that the temperatures of the orifices are known. I prefer to provide a heater so that the temperature of at least one of the orifices is at a set point. Another heater may be provided to assure that the sample is kept at a temperature above its dew point as the sample passes through the monitor.

Other objects and advantageous of the invention will become apparent from a description of certain present preferred embodiments thereof which are shown in the figures.

DETAILED DESCRIPTION OF THE PREFERRED EMBODIMENTS

Figure 1:
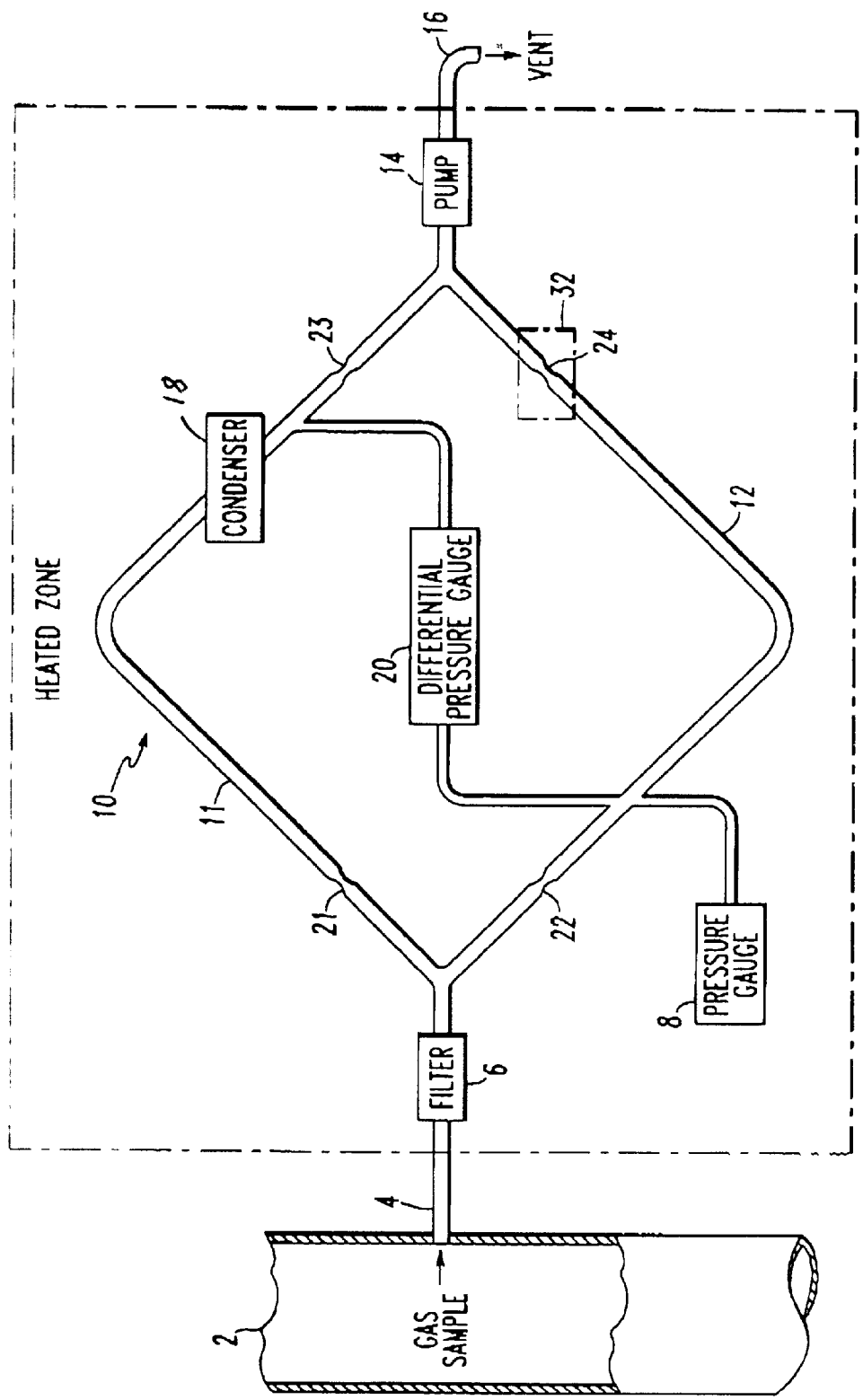
FIG. 1 is a schematic of a first present preferred embodiment of my gas concentration monitor for relatively high concentrations.
Figure 2:
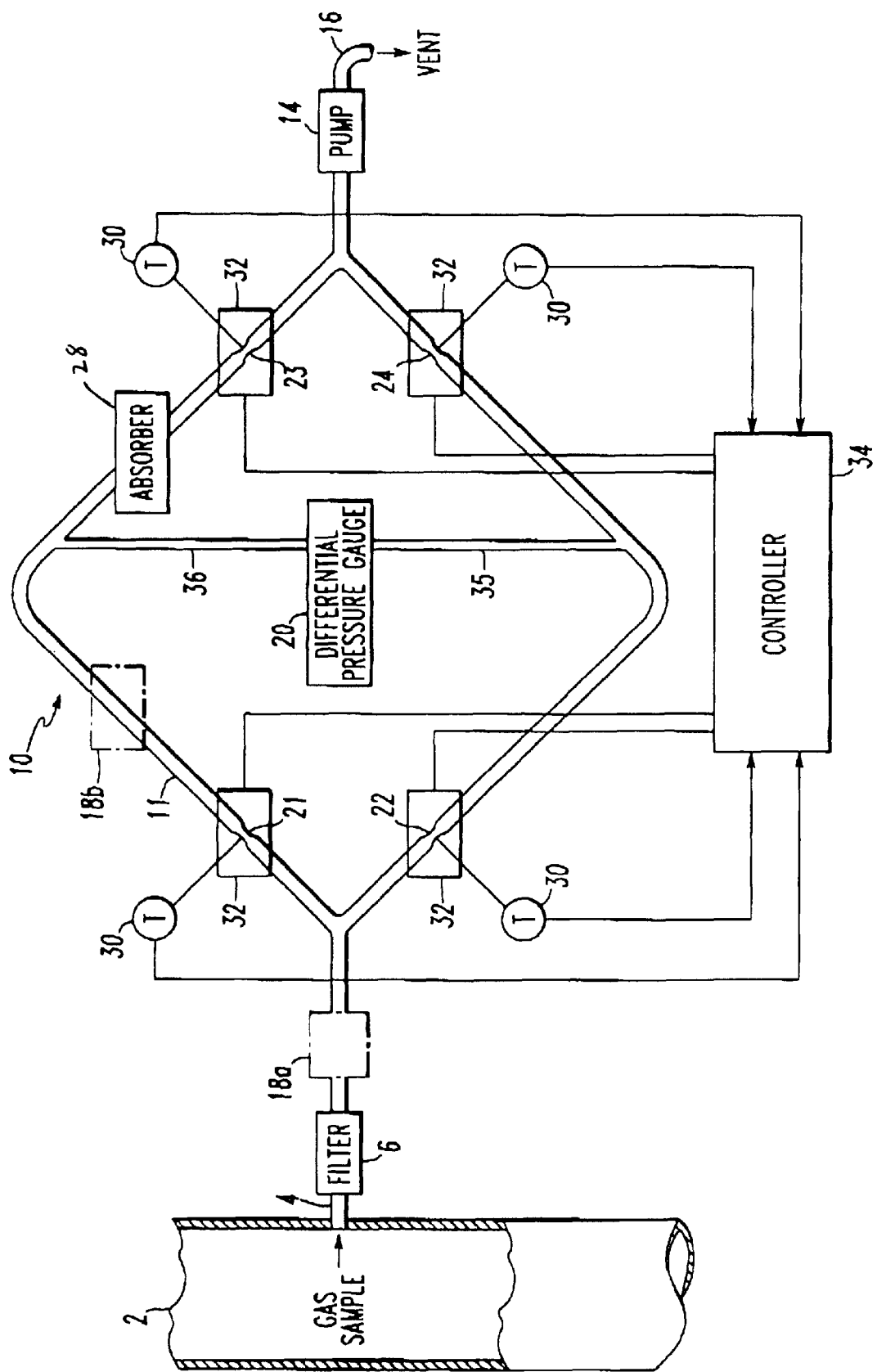
FIG. 2 is a schematic view of a second present preferred embodiment of my gas concentration monitor.

Referring to FIGS. 1 and 2, a gas sample is drawn from conduit 2 by an input pipe or probe 4. The probe could be the type of probe which is typically used for emissions sampling. Examples of such a probe are disclosed in my U.S. Pat. Nos. 5,440,217 and 5,297,432. The sample is passed through a filter 6 which removes particulates. The filtered sample is then directed into a bridge 10. The bridge is comprised of a first leg 11 and a second leg 12. In each leg there is an entry orifice 21, 22 and an exit orifice 23, 24. The sample is drawn through the bridge 10 by a pump 14 which then directs the sample through an exhaust pipe 16 to vent. The pump can be located on either the input side or the output side of the bridge. All of the orifices 21, 22, 23 and 24 are set up so that pressure in legs 10 and 12 is the same when the gas of interest is not present so that the differential pressure at gauge 20 is zero. This can be accomplished in several ways. All of the orifices can be exactly the same size. The orifices may be different sizes and one or more heaters could be provided to heat at least one orifice. In FIG. 1 optional heater 32 is shown in chainline around orifice 24. Another option is to provide a mechanical means for changing the size of one or more orifices. I further prefer to provide at least one heater to control the temperature of the entire monitor so that the sample is at a temperature above the dew point of the sample. In the embodiment shown in FIG. 1 this is done by placing the input, filter and bridge within a heated zone shown in dotted line. The heated zone is maintained by a heater (not shown) at a separate location. A condenser 18 or absorber 28 is provided in the first leg to remove the gas of interest. As indicated in FIG. 2, the leg may have both a condenser 18b (shown in dotted line) and an absorber 28. A differential pressure gauge 20 is connected between the first leg 11 and second leg 12. The gauge is connected at a location in each leg which is between the input orifice 21 or 22 and the exit orifice 23 or 24. The bridge may be balanced by a variety of means. I prefer to provide a heater 32 at one of the orifices which can change the temperature of the sample passing through that orifice. In the embodiment of FIG. 2 a heater is shown at each orifice 21, 22, 23 and 24. Consequently, the bridge can be balanced by heating an orifice. It is also possible to provide an orifice which has a mechanical device like a shutter that can change the size of the opening. Then the bridge can be balanced by changing the orifice size or by changing both the orifice size and orifice temperature. Yet, another option is to carefully create the orifices so that they are critical orifices. One could design the bridge to permit an orifice to be replaced to achieve a balanced system or provide a plurality of orifices which could be selected at a single location in much the same manner as one selects among several lens on a microscope by turning a dial.

If the monitor is being used to measure high concentrations of a gas, that is concentrations of 1% or higher, it is not necessary to obtain a perfect balance. A minor imbalance could cause a small error in the reading which is not significant for the purpose for which the monitor is being used. It is also possible to account for any imbalance by addition or subtraction.

The addition of an absolute pressure gauge 8 shown in FIG. 1 will allow the user to adjust the results if there is a change in the barometric pressure of the sample or changes in the filter such as partial clogging which change the absolute pressure of the entering sample. This can be particularly important if high accuracy is required.

During operation the gas of interest is removed from the sample as it passes through one leg of the bridge. In the embodiments of FIGS. 1 and 2 removal occurs in the upper leg 11. Since the condenser or absorber is removing the gas of interest from the first line 11, the pressure in that line will be lower than the pressure in the second line 12 which contains the gas of interest. Therefore, a differential pressure will exist between the first leg 11 and the second leg 12 which corresponds to the amount of gas removed from the first leg. Hence, one can calculate from the differential pressure reading on gauge 20 the concentration of the gas removed from leg 11 which is the concentration of that gas in the sample provided that the condenser or absorber removes all of the gas of interest.

EXAMPLE 1

The operation of the gas monitor can be further understood in the context of the following example. Suppose the gas sample contains water vapor and we wish to know the concentration of that water vapor. Gas samples are drawn through the bridge by pump 14 at a flow rate of 10 cc/min. The differential pressure gauge 20 provides a reading of 10 inches of water in a column which can be written 10" wc. From this information we are able calculate the concentration of water vapor.

A sample containing water is drawn through the bridge in an effort to measure the concentration of water in the sample. All regions of the conduits through which the sample passes are at a temperature above the dew point of the sample. The inlet pressure into the bridge is 400" wc. absolute and the outlet pressure is 40" wc. absolute. Orifices 21 and 22 are the same size in this example. Orifices 23 and 24 are the same size, but larger than orifices 21 and 22. Such sizing is not required but simplifies the relationships and makes the calculations easier. When the condenser is turned off no water is removed, the differential pressure gauge reads zero and the pressure in the condenser is 100" wc. absolute. All areas of the monitor are above the dew point of the sample so that no condensation occurs except in the condenser. After the condenser is turned on the differential pressure gauge reads 10" wc. This indicates that the pressure in the condenser is 90" wc. absolute. Because the orifices are critical, flow can be represented by $$Flow = P/\sqrt{T}$$

where P is the high side absolute pressure and T is the absolute temperature of the sample. Since T is held constant the pressure is directly related to flow. Because the orifices are critical there is a linear relationship between flow and pressure. An absolute pressure drop of 10" wc. corresponds to a 10% pressure drop since the beginning pressure was 100" wc. Consequently, the 10% pressure drop indicates that 10% of the sample has been removed. If the condenser has removed all of the water from the sample then the original sample contained 10% water.

It is not necessary for the condenser to remove all the moisture from the sample if the temperature of the sample leaving the condenser is known. One can assume that the sample is saturated as it leaves the condenser. The amount of moisture still in the sample can be determined from a look-up table which gives water content of a saturated gas at specific temperatures. That percentage water content is then added to the percent of water content removed by the condenser as determined by the differential pressure gauge reading. The sum of those values is the total concentration of water in the sample.

Because it is not necessary for the condenser to remove all of the moisture from the sample, one can cool the condenser to higher temperatures. Less time is required to remove water from the sample which allows the monitor to cycle faster. Finally, because less water is removed the condenser tank can be emptied less often.

In the second embodiment shown in FIG. 2 I provide an absorber 28 to remove the gas of interest. This absorber would be a column containing a media which absorbs the gas of interest. For example, if one desired to remove $CO_2$, then the absorber could be filled with a sodium hydrate asbestos absorbent such as ASCARITE absorbent material available from Thomas Scientific of Sweetsboro, N.J. Since ASCARITE material also removes water, the differential pressure readings would be a function of the concentration of the $CO_2$ gas absorbed and the water absorbed. To determine only $CO_2$ content, one can provide a condenser 18a which removes all water from the sample in front of the bridge in conduit 4. A differential pressure reading using lines 35 and 36 would indicate the amount of $CO_2$ removed. Another option is to provide two condensers 18a and 18b, one in conduit 4 and a second one in leg 11. In this system the condenser 18a in conduit 4 would be cycled on and off while the condenser 18b in leg 11 would be on continuously. When the first condenser is, on the second condenser would remove nothing and the absorber would remove $CO_2$. When the first condenser is off the second condenser 18b and absorber 28 would remove both water and $CO_2$. From the differential pressure readings of the two modes one could calculate the amount of water and the amount of $CO_2$ present in the sample. Although in FIG. 2 I show a single absorber and a two optional condensers and in the embodiment of FIG. 1 there is only one condenser it should be understood that multiple absorbers or multiple condensers or combinations thereof could be provided to measure the concentration of multiple gases. The choice and number of condensers and absorbers that are used will depend upon the gas or gases to be removed. If one wanted to remove water and sulfur dioxide one could use a monitor similar to that shown in FIG. 2. A condenser 18a in conduit 4 removes the water. Sulfur dioxide could be removed by using either a condenser 18a or an absorber 28.

In the embodiment of FIG. 2, I provide a temperature gauge 30 and a heater 32 for each orifice 21, 22, 23 and 24. The temperature gauges 30 are connected to controller 34. That controller is connected to each of the heaters 32. When the temperature gauge indicates that the temperature of a particular orifice has dropped below the desired temperature, the controller will direct the heater at that orifice to heat the orifice until the desired temperature is reached. Similarly, if the bridge is not balanced a selected orifice or orifices can be heated until both lines 11 and 12 are balanced and the differential pressure read by gauge 20 is zero. Another option is to omit the heaters and use only the temperature gauges. If that is done one must account for any temperature differences in calculating the gas content from the differential pressure reading.

The orifices should be such that orifices 21 and 23 produce the same ratio of input pressure and output pressure and orifices 22 and 24 produce the same ratio of input pressure and output pressure but the ratio need not be the same for all four orifices. I prefer to make orifices 21 and 22 to have a diameter which is about half the diameter of orifices 22 and 24. The restrictions at the orifices 21, 22, 23 and 24 preferably range in size from 0.001 to 0.01 inches in diameter. However, larger or smaller orifices could be used. By selecting small orifices, the volume can be kept low and the sample size would accordingly be small. This is important since it reduces temperature gradients, required pump size and the demand on the condenser and the absorbing media. Also, since the sample oftentimes has to be filtered before measurement, the lower flow provides for longer filter life. Having restrictions operating in the critical mode also provides a linear response to the change in flow value.

The bridge configuration allows ppm sensitivity to be reached by a readily available differential pressure gauge with a one inch water column full scale. More or less sensitivity may be achieved by changing the full scale value in the differential pressure gauge.

Providing a heated zone or individual heaters to maintain the restrictions at a fixed temperature will enable the device to produce a consistent response as well as adjust for a small difference in the orifices. Of further importance is the need for the condenser and/or absorbing media not to have a significant pressure drop or at least if it does have a significant pressure drop in respect to the differential pressures being measured, then it is important that the pressure drop is known. One can calculate the concentration by accounting for this pressure drop using simple addition or subtraction.

Although I have shown and described certain present preferred embodiments of my gas concentration monitor and method of measuring gas concentration, it should be distinctly understood that the invention is not limited thereto, but may be variously embodied within the scope of the following claims.

I claim:

1. A gas concentration monitor for measuring concentration of a portion of a gas mixture comprised of:
   a. an input line which receives a gas sample that contains a plurality of different gases, said gas sample including the portion of measurement interest;
   b. a gas flow bridge configuration having gas conveying conduit legs connected to the input line the bridge comprised of:
      i. a first leg connected to the input line having an entry orifice and an exit orifice through which a portion of the gas sample may flow;
      ii. a second leg connected to the input line having an entry orifice and an exit orifice through which a second portion of the gas sample may flow;
   c. a pump connected to the first leg and to the second leg for moving the sample through the bridge;
   d. a gas removal device connected to one leg of the bridge between the entry orifice and the exit orifice of that leg, the gas removal device being able to remove at least one of the plurality of different gases from the gas sample; and
   e. a differential pressure gauge connected between the first leg and the second leg at locations between the entry orifice and the exit orifice of each leg.

2. The gas concentration monitor of claim 1 also comprising a filter attached to the input line.

3. The gas concentration monitor of claim 1 also comprising a temperature gauge connected to provide a temperature of at least one orifice.

4. The gas concentration monitor of claim 1 also comprising at least one heater positioned to heat at least one of the orifices.

5. The gas concentration monitor of claim 4 also comprising a temperature gauge connected to provide a temperature of at least one orifice and a controller connected to the temperature gauge and to the at least one heater.

6. The gas concentration monitor of claim 1 also comprising a heater positioned to maintain the sample at a temperature above its dew point as the sample passes through the monitor.

7. The gas concentration monitor of claim 1 also comprising at least one heater positioned to heat all of the orifices.

8. The gas concentration monitor of claim 1 also comprising at least one heater positioned to heat at least one of the orifices and a temperature gauge attached to each of the orifices.

9. The gas concentration monitor of claim 8 also comprising a controller attached to the heater and each temperature gauge, the controller activating the heater in response to the temperature gauge for keeping each orifice at a controlled temperature.

10. The gas concentration monitor of claim 1 also comprising a pressure gauge attached to one leg of the bridge.

11. The gas concentration monitor of claim 1 wherein the gas removal device is a condenser.

12. The gas concentration monitor of claim 11 also comprising a second condenser connected to the input line.

13. The gas concentration monitor of claim 11 also comprising a absorber attached to the leg of the bridge to which the condenser is attached.

14. The gas concentration monitor of claim 1 wherein the gas removal device is an absorber.

15. A method of monitoring concentration of at least one particular gas in a sample containing a plurality of gases via a gas analysis apparatus, said gas sample including a portion of measurement interest having at least one gas to be removed from said gas sample and a complementary portion to be discharged from said apparatus comprising:
   a. dividing the sample into a first portion and a second portion;
   b. drawing the sample through a gas flow bridge configuration having gas conveying conduit legs comprised of:
      i. a first leg having an entry orifice and an exit orifice through which the first portion of the gas sample is directed; and
      ii. a second leg having an entry orifice and an exit orifice through which the second portion of the gas sample is directed;
   c. removing from the first leg the at least one particular gas whose concentration is to be measured;
   d. determining a temperature of at least one of the orifices;
   e. measuring a differential pressure between the first leg and the second leg; and
   f. calculating the concentration of the at least one particular gas which was removed based upon the differential pressure.

16. The method of claim 15 also comprising the step of filtering the sample.

17. The method of claim 15 wherein the temperature of at least one of the orifices is controlled by heating those orifices.

18. The method of claim 15 wherein the temperature of at least one of the orifices is determined by use of a temperature gauge.

19. The method of claim 15 also comprising maintaining the sample at a temperature above its dew point as the sample passes into and through the bridge.

20. The method of claim 15 also comprising the steps of monitoring temperatures of at least one of the orifices and maintaining at least one of the orifice at a controlled temperature.

21. The method of claim 15 also comprising the step of monitoring the temperatures of the orifices and accounting for any temperature differences in calculating the concentration of the at least one gas which was removed based upon the differential pressure.

22. The method of claim 15 wherein the at least one gas is removed by condensation.

23. The method of claim 22 wherein the condensation occurs in a condenser through which the first portion of the sample passes and the condenser creates a pressure drop and also comprising the steps of measuring the pressure drop and accounting for that pressure drop in calculating the concentration of the at least one gas that was condensed.

24. The method of claim 15 wherein the at least one gas is removed by absorption.

25. The method of claim 15 wherein two gasses are removed from the sample, one gas being removed by condensation and a second gas being removed by absorption.

* * * * *